United States Patent [19]
Uhlmann et al.

[11] Patent Number: 5,520,905
[45] Date of Patent: May 28, 1996

[54] COSMETIC OR DERMATOLOGICAL PREPARATION COMPRISING DELTA-AMINOLEVULINIC ACID CONTENT AS AN ACTIVE INGREDIENT

[75] Inventors: Beate Uhlmann; Tobias Mann, both of Hamburg; Heinrich Gers-Barlag, Kummerfeld; Gerhard Sauermann, Wiemersdorf, all of Germany

[73] Assignee: Beiersdorf Aktiengesellschaft, Hamburg, Germany

[21] Appl. No.: 260,843

[22] Filed: Jun. 16, 1994

[30] Foreign Application Priority Data

Jun. 24, 1993 [DE] Germany .......................... 43 20 871.1

[51] Int. Cl.$^6$ ....................................................... A61K 7/42
[52] U.S. Cl. ................... 424/59; 424/60; 514/561
[58] Field of Search ....................... 424/59, 60; 514/561

[56] References Cited

U.S. PATENT DOCUMENTS

| | | | |
|---|---|---|---|
| 4,568,665 | 2/1986 | Mitchell | 514/9 |
| 5,211,938 | 5/1993 | Kennedy et al. | 424/7.1 |

FOREIGN PATENT DOCUMENTS

| | | |
|---|---|---|
| 202778 | 11/1986 | European Pat. Off. . |
| 2728242 | 1/1979 | Germany . |
| 91/01727 | 2/1991 | WIPO . |
| 92/09635 | 6/1994 | WIPO . |

*Primary Examiner*—C. Warren Ivy
*Assistant Examiner*—Evelyn Huang
*Attorney, Agent, or Firm*—Sprung Horn Kramer & Woods

[57] ABSTRACT

A cosmetic or dermatological preparation comprising δ-aminolevulinic acid as an active ingredient.

20 Claims, No Drawings

COSMETIC OR DERMATOLOGICAL PREPARATION COMPRISING DELTA-AMINOLEVULINIC ACID CONTENT AS AN ACTIVE INGREDIENT

DESCRIPTION

The invention in question concerns cosmetic and dermatological preparations. The invention mainly concerns preparations which alleviate the adverse effects caused by exposure to light, particularly exposure to ultra-violet light and preparations which forestall such damage i.e. act as a preventative against such damage when applied before exposure to light, particularly exposure to ultra-violet light.

The harmful effects of the sun's ultra-violet radiation on the skin is generally well-known. While rays with a wave length of less than 290 nm (the so-called UVC range) are absorbed by the ozone layer in the earth's atmosphere, rays in the range between 290 nm and 320 nm, the so-called UVB range, cause erythema, a simple sun-burn or even light to severe burning.

The erythema effect is at a maximum with sunlight in a narrower range around 308 nm.

A number of compounds are known to protect against UVB radiation. These are derivatives of 3-benzylidene camphor, 4-aminobenzoic acid, cinnamic acid, salicylic acid, benzophenon and 2-phenylbenzimidazol.

Filter substances for radiation in the range between 320 nm and approx. 400 nm, the co-called UVA range, are also important as this radiation can also cause adverse effects. UVA radiation damages the elastic and collagenic fibres of the connective tissue which causes premature aging of the skin and has been found to cause a number of photo-toxic and photo-allergenic reactions. Furthermore, the damaging effect of UVB radiation can be exacerbated by UVA radiation.

Certain derivatives of dibenzoylmethane are predominantly used to protect against rays in the UVA range. However, UV radiation can also cause photo-chemical reactions where the photo-chemical reaction products attack the skin's metabolism.

Photo-chemical reaction products of this type are generally radical compounds, e.g. hydroxy radicals. Undefined radical photo products, which occur in the skin itself may also cause uncontrolled reactions on account of their high reactivity. Furthermore, UV radiation can also cause the appearance of singlet oxygen, a non-radical activated state of the oxygen molecule, in addition to short-lived epoxides etc. For example, compared with the triplet oxygen generally present (radical ground state), singlet oxygen is characterised by an increase in reactivity, although activated, reactive (radical) triplet states of the oxygen molecule also exist.

Antioxidants and/or radical inhibitors can be incorporated into cosmetic and/or dermatological formulations to prevent these reactions.

It is known that certain types of photodermatosis can be triggered by certain emulsifiers and also by various types of fat with simultaneous exposure to sunlight. These types of photodermatosis are called acne aestivalis.

The compounds used as light protection agents in cosmetic and dermatological light protection formulations, some of which are mentioned above, are notable for their satisfactory light protection properties. However, a disadvantage of these products is that sometimes it has been difficult to incorporate them satisfactorily into such formulations.

It has already been suggested that Vitamin E, a substance known to have an anti-oxidant action, should be used in light-protection formulations, but here too, the results have been far less satisfactory than expected.

An object of the present invention is therefore to provide cosmetic and dermatological substances and preparations containing active substances which would guarantee reliable protection from ultra-violet radiation and/or prevent the adverse effects caused by exposure to UV, alleviate existing damage or cure it completely.

In particular it is an object of the present invention to provide cosmetic and dermatological substances and preparations containing active substances which would counteract the aging of the skin which is caused or exacerbated by exposure to UV.

Finally it is an object of the present invention to provide cosmetic and dermatological substances and preparations containing active substances which would counteract acne aestivalis.

A person skilled in the art could not predict—and this is the premise for the solution to these problems—that cosmetic or dermatological preparations comprising δ-aminolevulinic acid as an active ingredient would remedy the problems with the current state of the art.

δ-aminolevulinic acid (also called δ-ALA, 5-amino-4-oxopentanoic acid, δ-amino-γ-keto-valeric acid) has the following structure:

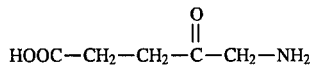

δ-aminolevulinic acid is an intermediate product of the biosynthesis of porphyrin and is formed during the citric acid cycle.

Heretofore, it was not known how to incorporate δ-aminolevulinic acid into cosmetic or dermatological formulations.

B. Ortel, A. Tanew and H. Hönigsmann (J. Photochem. Photobiol. B: Biol., 17 (1993), pp. 273–278) explain that administering δ-aminolevulinic acid externally to tumour cells induces the biosynthesis of porphyrins. The increased photosensitivity caused by the increase in porphyrin concentration facilitates the killing of these tumour cells by means of radiation with light of the appropriate wave-length.

However, a person skilled in the art and with knowledge of this document could not have arrived at the invention being submitted in this case.

Particularly valuable preparations are also obtained by combining δ-aminolevulinic acid with antioxidants.

The antioxidants according to the invention may usefully be selected from the standard group of cosmetic and dermatological antioxidants, particularly the group consisting of tocopherols and their derivatives, particularly α-tocopherol and/or α-tocopheryl esters, especially α-tocopherylacetate, in addition to sesame oil, bile acid derivatives such as methyl, ethyl, propyl, amyl, butyl and lauric gallate, the coniferylbenzoate of benzoin, nordihydroguaiacinic acid, nordihydroguaiaretic acid, butylhydroxyanisole, butylhydroxytoluol, ascorbic acid, citric acid, phosphoric acid, lecithin, trihydroxybutyrophenon, carotenes, vitamin A and its derivatives, particularly retinylpalmitate, ascorbic acid, ascorbylpalmitate, dilaurylthiodipropionate, distearylthiodipropionate, monoisopropylcitrate, thiodipropionic acid and EDTA and EDTA derivatives.

It is preferable to select the antioxidants according to the invention from the group of tocopherols and their derivatives.

Tocopherols, also called vitamin E, are derived from the parent substance tocol ((2-methyl-2-(4,8,12-trimethyltridecyl)-chroman-δ-ol) and have the following structures:

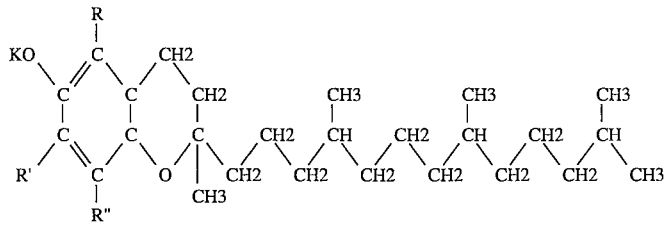

Here K represents either H or an acyl group independently of one another, R, R' and R" mean H or a methyl group, e.g.:

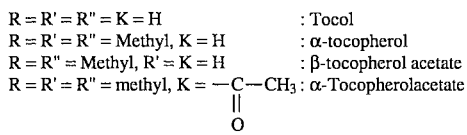

and other variations. In these esters, K represents the acyl group as follows:

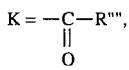

whereby R"" can represent an alkyl or alkenyl group. R""=methyl is particularly common.

In addition to the most frequently naturally occurring and important α-tocopherols there is also the configuration 2R, 4'R, 8'R. Occasionally, it is also called RRR-α-tocopherol.

The preferred tocopherol derivatives in accordance with the invention are α-tocopherol and its esters, especially α-tocopheryl-acetate.

While U.S. Pat. No. 4,144,325 and U.S. Pat. No. 4,248,861 and many other documents describe the use of vitamin E in cosmetic and dermatological light protection formulations, the combinations in accordance with the invention were previously unknown. Furthermore, the current state of the art does not provide any indications of the direction taken by the invention submitted in this instance.

Surprisingly, δ-aminolevulinic acid has been found to counteract the processes which play a role in the degeneration of the skin caused or exacerbated by ultra-violet light.

Nor could anyone have predicted that δ-aminolevulinic acid and/or cosmetic or dermatological preparations comprising δ-aminolevulinic acid as an active ingredient and/or the combinations according to the invention which consist of δ-aminolevulinic acids and at least one other substance selected from the antioxidant group, particularly tocopherols and tocopherylester, would be more effective in providing protection against the adverse effects of UV radiation as an antioxidant as a radical inhibitor in preventing the bonding of damaging photo products with lipids, DNS and proteins than preparations based on the known state of the art. Nor could anyone have predicted that δ-aminolevulinic acid and/or cosmetic or dermatological preparations comprising δ-aminolevulinic acid as an active ingredient and/or the combinations according to the invention which consist of δ-aminolevulinic acids and at least one other substance selected from the antioxidant group, particularly tocopherols and tocopherylester, would have sufficient stability for the application would lead to skin-compatible products would not attack the skin's own microorganism flora would counteract light-induced aging of the skin would counteract acne aestivalis.

In particular, no one could have predicted that δ-aminolevulinic acid and/or cosmetic or dermatological preparations comprising δ-aminolevulinic acid as an active ingredient and/or the combinations according to the invention which consist of δ-aminolevulinic acids and at least one other substance selected from the antioxidant group, particularly tocopherols and tocopherylester, would be notable for a marked delayed action.

Furthermore, the δ-aminolevulinic acid and/or cosmetic or dermatological preparations comprising δ-aminolevulinic acid as an active ingredient and/or the combinations according to the invention which consist of δ-aminolevulinic acids and at least one other substance selected from the antioxidant group, particularly tocopherols and tocopherylester, are particularly suitable for penetrating deeper layers of skin where they can display their effectiveness to particular advantage.

In addition, the δ-aminolevulinic acid and/or cosmetic or dermatological preparations comprising δ-aminolevulinic acid as an active ingredient and/or the combinations according to the invention, which consist of δ-aminolevulinic acids and at least one other substance selected from the antioxidant group, particularly tocopherols and tocopherylester, are also particularly suited for use as a strategic prophylactic for and/or treatment of skin damage caused by UV.

The use of δ-aminolevulinic acid and/or cosmetic or dermatological preparations comprising δ-aminolevulinic acid as an active ingredient and/or the combinations according to the invention, which consist of δ-aminolevulinic acids and at least one other substance selected from the antioxidant group, particularly tocopherols and tocopherylester, to protect the skin against the harmful effects of ultraviolet light is also in accordance with the invention.

Amazingly, it was found that δ-aminolevulinic acid and/or cosmetic or dermatological preparations comprising δ-aminolevulinic acid as an active ingredient and/or the combinations according to the invention, which consist of δ-aminolevulinic acids and at least one other substance selected from the antioxidant group, particularly tocopherols and tocopherylester, can inhibit photochemically produced radicals, provide protection against uncontrolled oxidation processes which are photochemically induced and even quench singlet oxygen, i.e. convert it to the triplet ground state by a physicochemical process. Substances with this property are also described as quenching agents.

Therefore the use of δ-aminolevulinic acid and/or cosmetic or dermatological preparations comprising δ-aminolevulinic acid as an active ingredient and/or combinations according to the invention which consist of δ-aminolevulinic acids and at least one other substance selected from the antioxidant group, particularly tocopherols and tocopherylester, as a radical inhibitor, an antioxidant and/or a quenching agent for photochemically produced reactive substances such as singlet oxygen, is also in accordance with the invention.

Cosmetic or dermatological preparations according to the invention may actually use a conventional formulation base and be used in the treatment of skin and/or hair as a part of a dermatological or cosmetic treatment. They should have a δ-aminolevulinic acid content of 0.1% to 10% by weight, but in particular 0.1% to 6% by weight as a percentage of the total weight.

Cosmetic or dermatological preparations in accordance with the invention should preferably contain 0.01% to 10% by weight, but in particular 0.1% to 6% by weight of one or several of the antioxidant group of substances, as a percentage of the total weight.

For use, the δ-aminolevulinic acid is applied in sufficient quantity in the usual way for cosmetics and dermatological products.

Cosmetic and dermatological preparations which come in the form of a sun-protection agent are particularly suitable. Ideally they will also contain at least one UVA filter or at least one UVB filter and/or at least one inorganic pigment.

Preparations applied to the skin after exposure to light, i.e. after-sun products, are also extremely suitable. It is up to the person skilled in the art to decide whether further UV filter substances should be used or not.

Preparations to prevent or treat acne aestivalis are also seen as an effective embodiment of the present invention.

Cosmetic preparations according to the invention for protecting the skin against UV radiation may come in different forms, as is generally the case for this type of preparation. They may come as an aqueous, alcohol or aqueous-alcohol solution, an emulsion of the water-in-oil type (W/O) or the oil-in-water type (O/W) or a multiple emulsion, e.g. of the water-in-oil-in-water type (W/O/W), a gel, a hydrodispersion, a solid stick or an aerosol.

The cosmetic preparations according to the invention may contain the type of cosmetic adjuvants generally used for such preparations, e.g. preservatives, bactericides, perfumes, foam-inhibitors, dyestuffs, pigments which act as a colorant, thickening agents, surface-active substances, emulsifiers, plasticising substances, moisturising and/or moisture-retention substances, fats, oils, waxes and other components generally used in cosmetic formulations such as alcohols, polyols, polymers, foam stabilisers, electrolytes, organic solvents or silicon derivatives.

Where the cosmetic or dermatological preparation is a solution or lotion, solvents which may be used are:

Water or aqueous solutions;

Oils such as triglycerides of caprio or caprylic acid, but preferably castor oil;

Fats, waxes and other natural and synthetic fatty compounds, preferably esters of fatty acids with alcohols with a low C number, e.g. with isopropanol, propylene glycol or glycerine or esters of fatty alcohols with alkanic acids with a low C number or with fatty acids;

Alcohols, diols or polyols with a low C number and their ethers, preferably ethanol, isopropanol, propylene glycol, glycerine, ethylene glycol, ethylene glycol monoethylether, ethylene glycol monobutylether, propylene glycol monomethylether, propylene glycol monoethylether, propylene glycol monobutylether, diethylene glycol monomethylether, diethylene glycol monoethylether and analogous products.

Mixtures of the above-mentioned solvents are used in particular. Water may be another component in the case of alcohol solvents.

Emulsions according to the invention, e.g. in the form of a sun protection cream, a sun protection lotion or a sun protection milk are useful and may contain the fats, oils, waxes and other fatty compounds mentioned, in addition to water and the usual type of emulsifier used for this type of formulation.

When a product is required which aims to prevent or alleviate acne aestivalis, it is useful according to the invention, to incorporate the δ-aminolevulinic acid or a combination of substances based on δ-aminolevulinic acid according to the invention, into hydro-dispersions or gels.

Cosmetic and dermatological preparations for skin treatment and skin care may be in the form of gels which, in addition to δ-aminolevulinic acid and the usual solvents used for it, also contain organic thickening agents such as gum arabic, xanthan gum, sodium alginate, cellulose derivatives, preferably methylcellulose, hydroxymethyl-cellulose, hydroxyethyl-cellulose, hydroxypropyl-cellulose, hydroxypropylmethyl-cellulose or inorganic thickening agents e.g. aluminium silicates such as bentonite or a mixture of polyethylene glycol and polyethylene glycol stearate or distearate. The percentage by weight of thickening agent in the gel may be between 0.1% and 30%, ideally between 0.5% and 15% by weight.

Gels according to the invention generally contain alcohols with a low C number, e.g. ethanol, isopropanol, 1,2-propanediol, glycerine and water and/or one of the above-mentioned oils in the presence of a thickening agent which is preferably silicon dioxide or an aluminium silicate in the case of oily alcohol gels, or a polyacrylate in the case of aqueous-alcohol or alcohol gels.

Hydrodispersions represent dispersions of a liquid, half solid or solid inner (discontinuous) lipid phase in an outer aqueous (continuous) phase.

Unlike O/W emulsions which are characterised by a similar phase arrangement, hydrodispersions are predominantly free of emulsifiers. Hydrodispersions represent metastable systems—as do emulsions—and tend to be converted into a state of two connected but discrete phases. In emulsions, the selection of a suitable emulsifer prevents phase separation.

In the case of hydrodispersions of a liquid lipid phase in an extremely aqueous phase, the stability of this type of system may be assured by creating a gel structure in the aqueous phase in which the lipid drops are in stable suspension.

Solid sticks according to the invention could contain natural or synthetic waxes, fatty alcohols or fatty acid esters for example. Lipsticks for lip care are preferable.

Conventional readily volatile, liquefied propellants such as hydrocarbons (propane, butane, isobutane), used singly or in combination, are suitable as propellants for spray cans containing cosmetic or dermatological preparations according to the invention. Compressed air may also be used effectively.

Of course a person skilled in the art knows that there are non-toxic propellants which would be suitable for this invention per se but which should not be used due to the harmful impact on the environment or other problems, in particular fluorocarbons and chlorofluorocarbons (CFCs).

In order to provide cosmetic preparations which protect the skin against the entire range of ultraviolet radiation, preparations according to the invention may also usefully contain substances which absorb UV-radiation in the UVB range, whereby the total amount of filter substances could be 0.1% to 30% by weight, preferably 0.5% to 10% by weight and in particular 1% to 6% by weight as a percentage of the total weight of the preparation. They may also be used as a sun protection agent.

The UVB filters may be oil-soluble or water-soluble. Examples of oil-soluble substances which could be used:

3-benzylidene camphor derivatives, preferably 3-(4-methylbenzylidene)camphor, 3-benzylidene-camphor;

4-aminobenzoic acid derivatives, preferably 4-(dimethylamino)-benzoic-acid (2-ethylhexyl)ester, 4-(dimethylamino)benzoic-acid-amylester;

Esters of cinnamic acid, preferably 4-methoxycinnamic-acid-(2-ethylhexyl)ester, 4-methoxycinnamic-acid-isopentylester;

Esters of salicylic acids, preferably salicylic acid(2-ethylhexyl)ester, salicylic acid(4-isopropylbenzyl)ester, salicylic acid-homomenthylester;

Derivatives of benzophenone, preferably 2-hydroxy-4-methoxybenzophenone, 2-hydroxy-4-methoxy-4'-methylbenzophenone, 2,2'-dihydroxy-4-methoxybenzophenone;

Esters of benzalmalonic acids, preferably 4-methoxybenzalmalonic-acid-di(2-ethylhexyl)ester;

2,4,6-trianilino-(p-carbo-2'-ethyl-1'-hexyloxy)-1,3,5-triazin.

Water-soluble substances which could be used:

Salts of 2-phenylbenzimidazol-5-sulphonic acid such as its sodium, potassium or triethanolammonium salt and the sulphonic acid itself;

Sulphonic acid derivatives of benzophenones, preferably 2-hydroxy-4-methoxybenzophenon-5-sulphonic acid and its salts.

Sulphonic acid derivatives of 3-benzylidene camphor such as 4-(2-oxo-3-bornylidene methyl)benzolsulphonic acid, 2-methyl-5-(2-oxo-3-bornylidenemethyl)sulphonic acid and its salts.

The combination of δ-aminolevulinic acid with one or more UV filters and/or cosmetic or dermatological preparations according to the invention and containing one or more UVB filters is also a subject matter of the invention.

It may also be useful to combine δ-aminolevulinic acid with UVA filters which have generally been a component of cosmetic and/or dermatological preparations in the past. These substances should preferably be derivatives of dibenzoylmethane, particularly 1-(4'-tert.butylphenyl)-3-(4'-methoxyphenyl)propane-1,3-dione and 1-phenyl-3-(4'-isopropylphenyl)propane-1,3-dione. These combinations and/or preparations containing these combinations are also a subject matter of the invention. The amounts used for the UVB combination may be used.

Further effective preparations may also be obtained when δ-aminolevulinic acid is combined with UVA and UVB filters.

Combinations of δ-aminolevulinic acid, one or more antioxidants and one or more UVA filters and one or more UVB filters are particularly effective according to the invention.

Cosmetic or dermatological preparations which contain δ-aminolevulinic acid may also contain inorganic pigments which are generally used in the cosmetic industry to protect skin against UVrays. The pigments in question are oxides of titanium, zinc, iron, zirconium, silicon, manganese, aluminium, cerium and mixtures of same, in addition to modifications whereby the oxides are the active agents. Pigments based on titanium dioxide are particularly effective.

Combinations of

δ-aminolevulinic acid and inorganic pigments

δ-aminolevulinic acid and antioxidants and inorganic pigments

δ-aminolevulinic acid and UV filter substances and inorganic pigments

δ-aminolevulinic acid and antioxidants and UV filter substances and inorganic pigments are also the subject matter of the invention. The quantities mentioned for the above combinations may be used.

The process used in the manufacture of cosmetic preparations according to the invention, which is characterised in that δ-aminolevulinic acid is incorporated into cosmetic or dermatological formulations by a method which is actually well-known, is also the subject matter of the invention.

The following examples should clarify the present invention without limiting it. All the given quantities, ratios and percentages relate to the weight and the overall volume and/or total weight of the preparations unless otherwise stated.

Example 1

| Sun Gel LF 4 (transparent) | Percentage by weight |
| --- | --- |
| Benzophenone-4 | 0.5 |
| Phenylbenzimidazolsulphonic acid | 1.3 |
| δ-aminolevulinic acid | 1.0 |
| Acrylamide/sodium acrylate-copolymer | 1.6 |
| Ethanol | 5.0 |
| Glycerine | 15.0 |
| NaOH (15%) | q.s. |
| Perfume, preservatives | q.s. |
| Water, fully demineralised | make up to 100.0 |

Example 2

| Hydrodispersion LF 6 | Percentage by weight |
| --- | --- |
| Octylmethoxycinnamate | 5.0 |
| Butylmethoxydibenzoylmethane | 1.0 |
| Phenyltrimethicone | 1.0 |
| Carbomer (Carbopol 981) | 1.0 |
| Hydroxypropylmethyl-cellulose | 0.2 |
| Butylene glycol | 3.0 |
| δ-aminolevulinic acid | 0.5 |
| Tromethamine | q.s. |
| EDTA solution (14%) | 0.5 |
| Ethanol | 5.0 |
| Perfume, preservatives | q.s. |
| Water, fully demineralised | make up to 100.0 |

Example 3

| Sun Milk O/W | Percentage by weight |
| --- | --- |
| Octylmethoxycinnamate | 5.0 |
| Butylmethoxydibenzoylmethane | 1.0 |
| Cetearylalcohol + PEG-40 castor oil + Sodiumcetearylsulphate | 2.5 |
| Glyceryllanolate | 1.0 |
| Laurylmethicon copolyol | 0.5 |
| Mineral oil (DAB 9) | 5.0 |
| Caprylic/capric triglyceride | 5.0 |
| Acrylamide/sodiumacrylate copolymer | 0.3 |
| Cyclomethicone | 2.0 |
| $TiO_2$ | 1.0 |
| δ-aminolevulinic acid | 1.0 |
| Glycerine | 3.0 |

-continued

| | |
|---|---|
| EDTA solution (14%) | 0.5 |
| Ethanol | 5.0 |
| Perfume, preservative | q.s. |
| Water, fully demineralised | make up to 100.0 |

Example 4

| Skin-care lotion W/O | Percentage by weight |
|---|---|
| Cyclomethicone | 3.0 |
| PEG-1-glycerine sorbitan oleostearate | 1.7 |
| PEG-7 hydrated castor oil | 6.3 |
| Mineral oil (DAB 9) | 13.0 |
| Caprylic/capric triglyceride | 13.0 |
| δ-aminolevulinic acid | 3.0 |
| Glycerine | 4.0 |
| $MgSO_4$ | 0.7 |
| Perfume, preservative | q.s. |
| Water, fully demineralised | make up to 100.0 |

Example 5

| Day-car skin cream O/W | Percentage by weight |
|---|---|
| PEG-5 Glycerylstearate | 2.00 |
| Glycerylstearate | 3.00 |
| Cyclomethicone | 3.00 |
| Caprylic/capric triglyceride | 3.00 |
| Cetylalcohol | 3.00 |
| Octylmethoxycinnamate | 2.50 |
| δ-aminolevulinic acid | 5.00 |
| Ethanol | 1.00 |
| Hyaluronic acid | 0.05 |
| Tocopherylacetate | 0.50 |
| Glycerine | 4.00 |
| Perfume, preservatives | q.s. |
| Water, fully demineralised | make up to 100.00 |

Example 6

| Sun Cream W/O | Percentage by weight |
|---|---|
| PEG-22-dodecyl glycol copolymer | 3.0 |
| Cetyl dimethicon copolyol | 2.0 |
| Cyclomethicone | 4.0 |
| Octylmethoxycinnamate | 7.0 |
| Methylbenzylidene camphor | 3.4 |
| Butylmethoxydibenzoylmethane | 1.0 |
| Mineral oil (DAB 9) | 4.0 |
| Caprylic/capric triglyceride | 4.0 |
| δ-aminolevulinic acid | 2.5 |
| Glycerine | 4.00 |
| Perfume, preservatives | q.s. |
| Water, fully demineralised | make up to 100.00 |

Example 7

| After Sun Lotion | Percentage by weight |
|---|---|
| Cetearylalcohol + PEG-40 castor oil + sodiumcetearylsulphate | 2.50 |
| Glycerylstearate SE | 0.60 |
| Mineral oil (DAB 9) | 4.00 |
| Caprylic/capric triglyceride | 2.00 |
| Sheabutter | 2.00 |
| Avocado oil | 2.00 |
| Tocopherylacetate | 3.00 |
| δ-aminolevulinic acid | 2.00 |
| Acrylamide/sodiumacrylate copolymer | 0.30 |
| Glycerine | 4.00 |
| Hyaluronic acid | 0.05 |
| Bisabolol | 0.05 |
| Perfume, preservatives | q.s. |
| Water, fully demineralised | make up to 100.00 |

The following experiment demonstrates the effective action of δ-aminolevulinic acid.

Experiment

The antioxidation action of δ-aminolevulinic acid was ascertained by chemiluminescence measurement. Chemiluminescence shows the oxidation processes in the skin and a reduction in chemiluminescence is synonymous with a reduction in oxidation processes.

Test Material: Acrylate gel with 5% by weight of δ-aminolevulinic acid (ALA)

Method: Measurement of chemiluminescence in hands before treatment and 3 hours after treatment with ALA and/or placebo (Gel without δ-aminolevulinic acid)

Test Subjects: 12 people, 4 male, 8 female.

Test Period: 3 days.

Application: ALA is measured out volumetrically (90 μl) and applied with a finger stall to the back of the right and/or left hand over a 5.6 cm×8 cm area. The placebo is applied to the back of the other hand. The application sites (right hand-left hand) are selected at random.

Test Procedure: 1st Day An area on the back of the hand between the base of the thumb and the metacarpal bone is marked and measured by reflection spectra. Chemiluminescence measurements before and after 30 seconds of UVA radiation using a UVA Spot (from H önle). Treatment with δ-aminolevulinic acid and placebo, both applied at the rate of 2 mg/cm². Measurements repeated 3 hours later.

2nd and 3rd Day The test procedure described above was carried out with 4 further test subjects.

Measurement conditions for LS 50: Synchron Modus, interval: 0 nm, range: 300–500 nm, ex slit: 4 nm, em slit: 3.5 nm, scan speed: 500 nm/min., 4% attenuator.

Results: 3 hours after treatment, there was a reduction of 11.8% in luminescence in the hands treated with ALA compared with the initial situation. As expected, there was almost no change in the hands treated with the placebo.

We claim:

1. A method of alleviating the skin from the damage resulting from exposure to the sun, which comprises applying thereto an amount effective therefor of a composition comprising a carrier and a cosmetically or dermatologically effective amount of δ-aminolevulinic acid.

2. A method according to claim 1, wherein the δ-aminolevulinic acid is present in about 0.01 to 10% by weight.

3. A method according to claim 1, wherein the δ-aminolevulinic acid is present in about 0.01 to 6% by weight.

4. A method according to claim 1, further containing an antioxidant.

5. A method according to claim 2, wherein the antioxidant is at least one member selected from the group consisting of a tocopherol or ester thereof, sesame oil, methyl, ethyl, propyl, amyl, butyl or lauryl gallate, the coniferylbenzoate of benzoin, nordihydroguaiacinic acid, nordihydroguaiaretic acid, butylhydroxyanisole, butylhydroxytoluol, ascorbic acid, citric acid, phosphoric acid, lecithin, trihydroxybutyrophenon, a carotene, vitamin A or a derivative thereof, retinyl palmitate, ascorbyl palmitate, dilaurylthiodipropionate, distearylthiodipropionate, monoisopropylcitrate, thiodipropionic acid and ethylenediaminetetraacetic acid or a derivative thereof.

6. A method according to claim 5, wherein the antioxidant is present in about 0.01 to 10% by weight.

7. A method according to claim 5, wherein the antioxidant is present in about 0.01 to 6% by weight.

8. A method according to claim 1, further containing a substance which absorbs UV radiation in the UVA or UVB range.

9. A method according to claim 5, further containing a substance which absorbs UV radiation in the UVA or UVB range.

10. A method according to claim 9, wherein each of the δ-aminolevulinic acid and antioxidant is present in about 0.1 to 6% by weight, the antioxidant is tocopherol or an ester thereof, and the composition further contains a substance which absorbs UV radiation in the UVA or UVB range.

11. In the exposure of skin to sunlight under conditions which would otherwise result in light to severe burning is improvement which comprises, applying thereto an amount effective therefor of a composition comprising a carrier and a cosmetically or dermaologically effective amount of δ-aminolevulinic acid, whereby the skin is protected from such burning.

12. A method according to claim 11, wherein the aminolevulinic acid is present in about 0.01 to 10% by weight.

13. A method according to claim 11, wherein the aminolevulinic acid is present in about 0.01 to 6% by weight.

14. A method according to claim 11, wherein the compositions further contains an antioxidant.

15. A method according to claim 12, wherein the antioxidant is at least one member selected from the group consisting of a tocopherol or ester thereof, sesame oil, methyl, ethyl, propyl, amyl, butyl or lauryl gallate, the coniferylbenzoate of benzoin, nordihydroguaicinic acid, nordihydroguaiaretic acid, butylhydroxyanisole, butylhydroxytoluol, ascorbic acid, citric acid, phosphoric acid, lecithin, trihydroxybutyrophenon, a carotene, vitamin A or a derivative thereof, retinyl palmitate, ascorbyl palmitate, dilaurylthiodipropionate, distearylthiodipropionate, monoisopropylcitrate, thiodipropionic acid and ethylenediaminetetraacetic acid or a derivative thereof.

16. A method according to claim 15, wherein the antioxidant is present in about 0.01 to 10% by weight.

17. A method according to claim 15, wherein the antioxidant is present in about 0.01 to 6% by weight.

18. A method according to claim 11, further containing a substance which absorbs UV radiation in the UVA or UVB range.

19. A method according to claim 15, further containing a substance which absorbs UV radiation in the UVA or UVB range.

20. A method according to claim 19, wherein each of the δ-aminolevulinic acid and antioxidant is present in about 0.1 to 6% by weight, the antioxidant is tocopherol or an ester thereof, and the composition further contains a substance which absorbs UV radiation in the UVA or UVB range.

* * * * *

UNITED STATES PATENT AND TRADEMARK OFFICE
CERTIFICATE OF CORRECTION

PATENT NO. : 5,520,905
DATED : May 28, 1996
INVENTOR(S) : Uhlmann, et al.

It is certified that error appears in the above-indentified patent and that said Letters Patent is hereby corrected as shown below:

Col. 11, line 19    After " the " insert --$\delta$--

Col. 11, line 21    After " the " insert --$\delta$--

Signed and Sealed this

Twenty-ninth Day of October 1996

Attest:

BRUCE LEHMAN

Attesting Officer    Commissioner of Patents and Trademarks